US010195002B2

(12) United States Patent
Kim

(10) Patent No.: US 10,195,002 B2
(45) Date of Patent: Feb. 5, 2019

(54) DEVICE AND METHOD FOR GENERATING DENTAL THREE-DIMENSIONAL SURFACE IMAGE

(71) Applicants: VATECH Co., Ltd., Gyeonggi-do (KR); VATECH EWOO Holdings Co., Ltd., Gyeonggi-do (KR)

(72) Inventor: Tae Woo Kim, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 255 days.

(21) Appl. No.: 15/037,421

(22) PCT Filed: Nov. 18, 2014

(86) PCT No.: PCT/KR2014/011067
§ 371 (c)(1),
(2) Date: May 18, 2016

(87) PCT Pub. No.: WO2015/072807
PCT Pub. Date: May 21, 2015

(65) Prior Publication Data
US 2016/0287359 A1   Oct. 6, 2016

(30) Foreign Application Priority Data
Nov. 18, 2013  (KR) .................. 10-2013-0139818

(51) Int. Cl.
*A61B 6/14* (2006.01)
*A61C 9/00* (2006.01)
(Continued)

(52) U.S. Cl.
CPC .......... *A61C 9/0053* (2013.01); *A61B 5/1079* (2013.01); *A61B 6/14* (2013.01);
(Continued)

(58) Field of Classification Search
CPC ......... A61C 9/00; A61C 9/0053; A61C 13/34; G06T 15/08; H04N 13/02; H04N 13/0203;
(Continued)

(56) References Cited

U.S. PATENT DOCUMENTS 6,196,715 B1    3/2001   Nambu et al.
8,750,450 B2 *  6/2014   Ulrici ................ A61B 6/14
                                                    378/38
(Continued)

FOREIGN PATENT DOCUMENTS

JP   2011-510685 A    4/2011
KR   10-1133503 B1    4/2012

OTHER PUBLICATIONS

European Patent Office, Extended European Search Report of corresponding EP Patent Application No. 14861968.7, dated Jun. 8, 2017.

*Primary Examiner* — Jurie Yun
(74) *Attorney, Agent, or Firm* — IP Legal Services, LLC

(57) ABSTRACT

The disclosure is related to a device and method for obtaining a complete and accurate three-dimensional surface image of a target object by registering a three-dimensional optical image with a volume data obtained by X-ray imaging. The device for generating a three-dimensional surface image for dentistry includes a three-dimensional imaging module including an optical camera which obtains a three-dimensional optical image of the target object and an X-ray imaging unit which obtains X-ray images of the target object in multiple directions, a reconstruction unit generating a volume data by reconstructing the X-ray images, and an image processing unit registering the three-dimensional optical image with the volume data and generating a three-dimensional surface image of the target object by substitut- (Continued)

ing a different portion of the three-dimensional optical image with a boundary of the volume data.

4 Claims, 4 Drawing Sheets

(51) Int. Cl.
    *H04N 13/204*     (2018.01)
    *G03B 42/02*     (2006.01)
    *G06T 19/00*     (2011.01)
    *A61B 6/00*     (2006.01)
    *A61B 5/107*     (2006.01)
    *A61C 13/34*     (2006.01)
    *G06T 15/08*     (2011.01)
    *G03B 35/00*     (2006.01)

(52) U.S. Cl.
    CPC ............ *A61B 6/4417* (2013.01); *A61B 6/466* (2013.01); *A61B 6/5247* (2013.01); *A61C 13/34* (2013.01); *G03B 42/02* (2013.01); *G06T 15/08* (2013.01); *G06T 19/00* (2013.01); *H04N 13/204* (2018.05); *A61B 6/463* (2013.01); *G03B 35/00* (2013.01)

(58) Field of Classification Search
    CPC ........... A61B 6/00; A61B 6/14; A61B 6/5247; A61B 6/4417; A61B 6/463; A61B 6/466; A61B 6/032
    USPC ............... 378/4, 63, 901; 382/128, 131, 132
    See application file for complete search history.

(56) References Cited

U.S. PATENT DOCUMENTS

| | | | |
|---|---|---|---|
| 8,798,346 B2 * | 8/2014 | Cizek | ........................ G06T 7/33 378/62 |
| 2003/0068079 A1 | 4/2003 | Park | |
| 2009/0316966 A1 | 12/2009 | Marshall et al. | |
| 2011/0008751 A1 | 1/2011 | Pettersson | |
| 2011/0044520 A1 | 2/2011 | Nakai et al. | |
| 2011/0268327 A1 | 11/2011 | Getto et al. | |
| 2012/0214121 A1 | 8/2012 | Greenberg | |
| 2012/0282572 A1 | 11/2012 | MacLeod et al. | |

* cited by examiner

DEVICE AND METHOD FOR GENERATING DENTAL THREE-DIMENSIONAL SURFACE IMAGE

CROSS REFERENCE TO RELATED APPLICATIONS

This application is a National Stage Patent Application of PCT International Patent Application No. PCT/KR 2014/011067 (filed on Nov. 18, 2014) under 35 U.S.C. § 371, which claims priority to Korean Patent Application No. 10-2013-0139818 (filed on Nov. 18, 2013), the teachings of which are incorporated herein in their entireties by reference.

BACKGROUND

1. Technical Field

The present disclosure relates to an apparatus and method for generating a three-dimensional surface image for dentistry, and more particularly, to an invention capable of obtaining a complete and accurate three-dimensional surface image of a target object by registering a three-dimensional optical image of the target object obtained by an optical camera with volume data or a rendering image of the target object obtained by an X-ray imaging unit.

2. Related Art

In general, in order to obtain an image of a surface of a target object, a method for obtaining a three-dimensional optical image of the target object using an optical camera is chiefly performed. Such a three-dimensional optical image is generated by measuring the distance from equipment measuring an external appearance of a target object to a surface of the target object. A major measurement method includes a laser scan method for radiating a laser to a target object, measuring the time taken for the laser to be reflected by the target object and then returned to measurement equipment, and generating an image of a surface of the target object by measuring the distance between the measuring equipment and the target object, a confocal microscopy structure method for illuminating a pattern using confocal microscopy and generating an image of a surface of a target object based on reflected location information, or a stereo photogrammetry method for measuring the distance to a target object using photos of a surface of the target object obtained at various angles and generating an image of the surface of the target object using the measured distance.

In a three-dimensional optical image using the optical camera, however, a surface of a target object is not smoothly formed. If a concave portion and a convex portion are present in the surface of the target object, in particular, in the case of an impression material or a plaster cast into which a patient dentition has been incorporated in order to fabricate a dental's prosthesis, it is difficult to accurately measure the distance due to a gap that light having straightness cannot reach and that is bent, such as a boundary surface between a teethridge and a tooth or an embrasure. Accordingly, there is a problem in that it is difficult to obtain a complete image of a surface of the target object.

SUMMARY

In order to solve the conventional problems, an object of the present invention is to provide an apparatus and method for generating a three-dimensional surface image for dentistry, which are capable of obtaining a three-dimensional surface image of a target object which has been perfectly and precisely represented by registering a three-dimensional optical image of the target object obtained by an optical camera with volume data or a rendering image of the target object obtained by an X-ray imaging unit.

An apparatus for generating a three-dimensional surface image for dentistry according to the present invention for achieving the object includes a three-dimensional imaging module including an optical camera which obtains a three-dimensional optical image of a target object and an X-ray imaging unit which obtains X-ray images of the target object in multiple directions; a reconstruction unit generating volume data by reconstructing the X-ray images; and an image processing unit registering the three-dimensional optical image with the volume data and generating a three-dimensional surface image of the target object by substituting a different portion of the three-dimensional optical image with the boundary of the volume data.

The apparatus for generating a three-dimensional surface image for dentistry may further include a rendering unit generating a rendering image of the target object by rendering the volume data. The image processing unit may generate the three-dimensional surface image of the target object by registering the three-dimensional optical image with the rendering image and substituting the different portion of the three-dimensional optical image with the rendering image.

The three-dimensional imaging module may include a turn table on which the target object is placed.

The optical camera may be installed on one side of the target object and may be any one of a laser scan method, a confocal microscopy method, and a stereo photogrammetry method.

The X-ray imaging unit may include an X-ray sensor and an X-ray emission source with the target object interposed between the X-ray sensor and the X-ray emission source.

The image processing unit may register the three-dimensional optical image with the volume data based on a coordinate system of the target object.

A method for generating a three-dimensional surface image for dentistry according to the present invention for achieving another object includes the steps of generating, by an optical camera, a three-dimensional optical image of a target object by imaging the target object in multiple directions (step 1); detecting, by an X-ray imaging unit, X-ray images of the target object in multiple directions and generating volume data by reconstructing the X-ray images (step 2); and generating a three-dimensional surface image of the target object by registering the three-dimensional optical image with the volume data and substituting a different portion of the three-dimensional optical image with the boundary of the volume data (step 3).

The method for generating a three-dimensional surface image for dentistry may further include the step of generating a rendering image by rendering the volume data prior to the step 3 after the step 2. The step 3 may include generating the three-dimensional surface image of the target object by registering the three-dimensional optical image with the rendering image and substituting the different portion of the three-dimensional optical image with the rendering image.

The step 1 may be performed by any one of a laser scan method, a confocal microscopy method, and a stereo photogrammetry method.

The apparatus for generating a three-dimensional surface image for dentistry according to the present invention has an advantage in that it can obtain a three-dimensional surface image in which a surface region of a target object, in particular, a detailed portion of an impression material or plaster cast into which a patient's dentition has been incorporated in order to fabricate a dental prosthesis, for example, a boundary surface between a teethridge and a tooth or an interproximal space has been represented accurately and precisely.

DESCRIPTION OF REFERENCE NUMERALS

Figure 1:
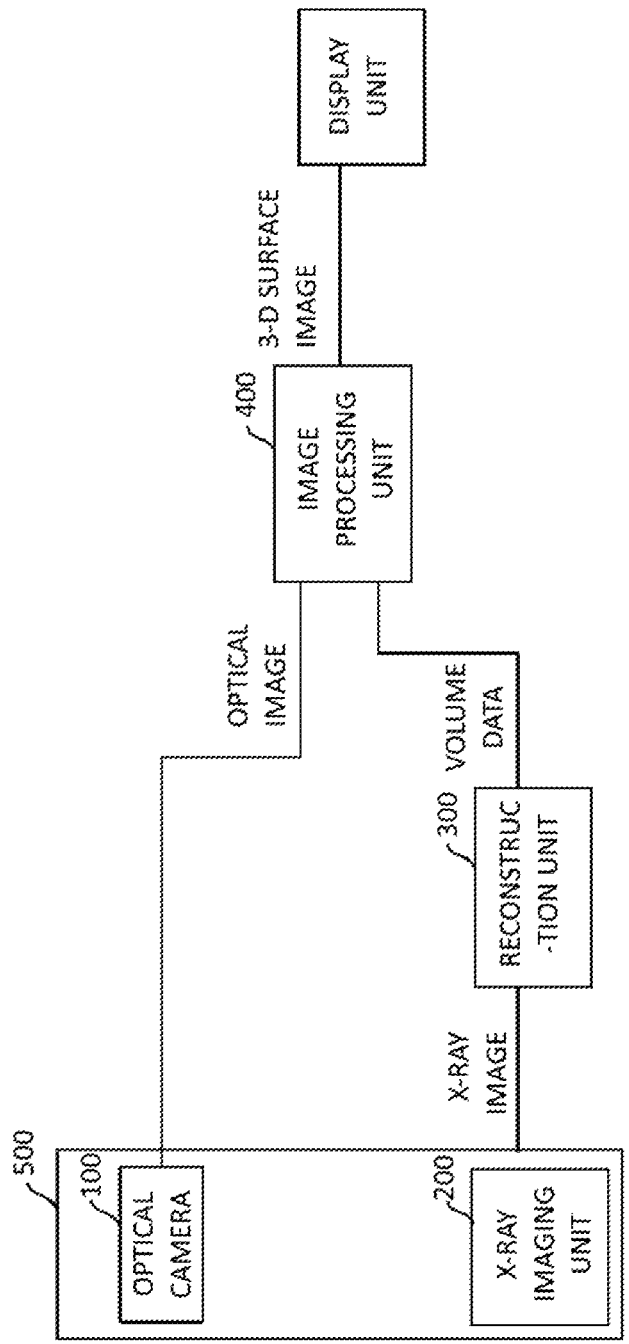
FIG. 1 is a block diagram of an apparatus for generating a three-dimensional surface image for dentistry in accordance with an embodiment of the present invention.

100: optical camera 300: reconstruction unit
200: X-ray Imaging unit 310: rendering unit
210: X-ray emission source 400: image processing unit
220: X-ray sensor 500: three-dimensional imaging module
230: X-rays 600: turn table

DETAILED DESCRIPTION

Hereinafter, preferred embodiments of the present invention will be described in detail with reference to the accompanying drawings. The following embodiments may be modified in various forms, and the scope of the present invention is not restricted by the following embodiments. An embodiment of the present invention is provided to clearly convey the technical spirit of the invention to a person having ordinary skill in the art.

FIG. 1 is a block diagram of an apparatus for generating a three-dimensional surface image for dentistry in accordance with an embodiment of the present invention.

As shown in FIG. 1, the apparatus for generating a three-dimensional surface image for dentistry in accordance with an embodiment of the present invention includes an optical camera 100, an X-ray imaging unit 200, a reconstruction unit 300, an image processing unit 400, and a three-dimensional imaging module 500. A display unit of FIG. 1 is an element for displaying a three-dimensional surface image generated the present invention. If the apparatus for generating a three-dimensional surface image for dentistry according to the present invention is implemented using a three-dimensional surface image display device, the display unit may be construed as being included in the category of the present invention.

The optical camera 100 obtains optical images of a target object in multiple directions for a three-dimensional optical image of the target object. The obtaining of the optical images of the target object by the optical camera 100 is performed using a laser scan method, a confocal microscopy method, or a stereo photogrammetry method, and is not limited to the above methods as long as optical images of the target object can be obtained.

In the laser scan method, after a laser is radiated to a target object, the time taken for the laser to be reflected by the target object and then returned to a measurement equipment is measured and an image of a surface of the target object is generated by measuring the distance between the measuring equipment and the target object. In the confocal microscopy method, a pattern is illuminated using confocal microscopy and an image of a surface of a target object is generated based on reflected location information. In the stereo photogrammetry method, the distance to a target object is measured using photos of a surface of the target object obtained at various angles and an image of the surface of the target object is generated using the measured distance.

An optical image of a target object obtained by the optical camera 100 shows a rough image of a surface of the target object. If a portion that is not smoothly formed and has a concave part and a convex part is included in the surface of the target object, in particular, in the case of an impression material or a plaster cast into which a patient's dentition has been incorporated in order to fabricate a dental prosthesis, a bent gap portion, such as a boundary surface between a teethridge and a tooth or an interproximal space, is present. In those portion, as the imaging device cannot receive a feedback of the incident laser or cannot image the illuminated pattern, the optical image cause a limit for expression details. Accordingly, an accurate representation of a surface image of the target object using the optical image is limited.

The X-ray imaging unit 200 includes an X-ray emission source 210 and an X-ray sensor 220. The X-ray imaging unit 200 obtains transmission images of a target object in multiple directions in such a way as to radiate X-rays to the target object using the X-ray emission source 210 and to detect X-ray images passing through the target object using the X-ray sensor. The X-ray emission source 210 and the X-ray sensor 220 forming the X-ray detector 200 are described later with reference to FIGS. 3 to 5.

The reconstruction unit 300 generates volume data by reconstructing X-ray images of multiple directions generated by the X-ray imaging unit 200. The volume data is obtained by placing data obtained from the spatial sequence of a two-dimensional cross image in different layers and reconstructing the data in a continuous gray level volume, and it represents a voxel model within a field of view (FOV) based on a difference between gray levels according to a CT number.

In order to obtain volume data having a clear gray level difference in an external boundary surface, a difference between the CT numbers of a target object and air needs to be great. Accordingly, it is preferred that a target object in the present invention is an impression material or a plaster cast made of a single material into which a patient's dentition has been incorporated, but is not limited thereto.

In an embodiment of the present invention, the image processing unit 400 generates three-dimensional optical images of a target object using optical images of multiple directions obtained by the optical camera 100, and generates a three-dimensional surface image by registering volume data corresponding to the coordinate system of the target object with a three-dimensional optical image corresponding to the coordinate system of the target object. To this end, a additional algorithm for generating the three-dimensional optical images of the target object from the optical images of the multiple directions may be embedded in the image processing unit 400. Alternatively, the algorithm may be embedded in the optical camera 100, and the optical camera 100 may generate the three-dimensional optical images of the target object. Furthermore, additionally, after registering the volume data with the three-dimensional optical image, the image processing unit 400 may generate a more accurate three-dimensional surface image by registering volume data when a distance deviation between the coordinate systems of the three-dimensional optical image and volume data becomes a minimum with the three-dimensional optical image again while moving the coordinate system of the volume data in a three-dimensional manner based on the optical image.

An optical image and volume data correspond to the results of the imaging of the same target object and thus may be matched up based on the coordinate system of the target object. A surface of the target object which is not clearly distinct based on a three-dimensional optical image is supplemented with the volume data. Accordingly, in the case of a concave portion and convex portion not smoothly formed in the surface of the target object, in particular, in the case of an impression material or plaster cast into which a patient's dentition has been incorporated in order to fabricate a dental prosthesis, a three-dimensional surface image in which the entire surface of the target object including a boundary surface between a teethridge and a tooth or an embrasure has been precisely represented can be obtained.

Although an optical image and volume data correspond to the results of the imaging of the same target object, a location where the target object is imaged is different and the optical image and the volume data may be partially different due to interference between the X-ray sensor and the optical camera. In this case, additionally, a more precisely represented three-dimensional surface image of the target object can be obtained by registering the other of the optical image and the volume data when a distance deviation between the optical image and the volume data becomes a minimum with one of the optical image and the volume data again, while moving the coordinate system of the other of them in a three-dimensional manner based on one of them.

In this case, the image processing unit 400 may include a rendering unit of FIG. 2 to be described later. After volume data corresponding to the coordinate system of a target object is registered with a three-dimensional optical image corresponding to the coordinate system of the target object, additionally, a three-dimensional surface image may be generated by registering volume data when a distance deviation between the coordinate systems of the three-dimensional surface image and volume data becomes a minimum with the three-dimensional optical image again while moving the coordinate system of the volume data in a three-dimensional manner based on a rendering image generated by the rendering unit. This may be easily understood through a description of FIG. 2 to be given later.

Furthermore, after registering the three-dimensional optical image and volume data of the target object, the image processing unit 400 generates a three-dimensional surface image by substituting a different portion of the three-dimensional optical image with the boundary of the volume data or a rendering image. In this case, the image processing unit 400 may properly adjust the color of the boundary portion of the substituted volume data or substituted rendering image in order to minimize a difference between the boundary of the substituted volume data or substituted rendering image and the remaining three-dimensional optical images other than the boundary of the substituted volume data or substituted rendering image.

The three-dimensional imaging module 500 includes the optical camera 100 and the X-ray imaging unit 200, and preferably includes a turn table for rotating a target object and a housing member for accommodating the optical camera, the X-ray imaging unit, and the turn table and shielding X-rays.

Figure 2:
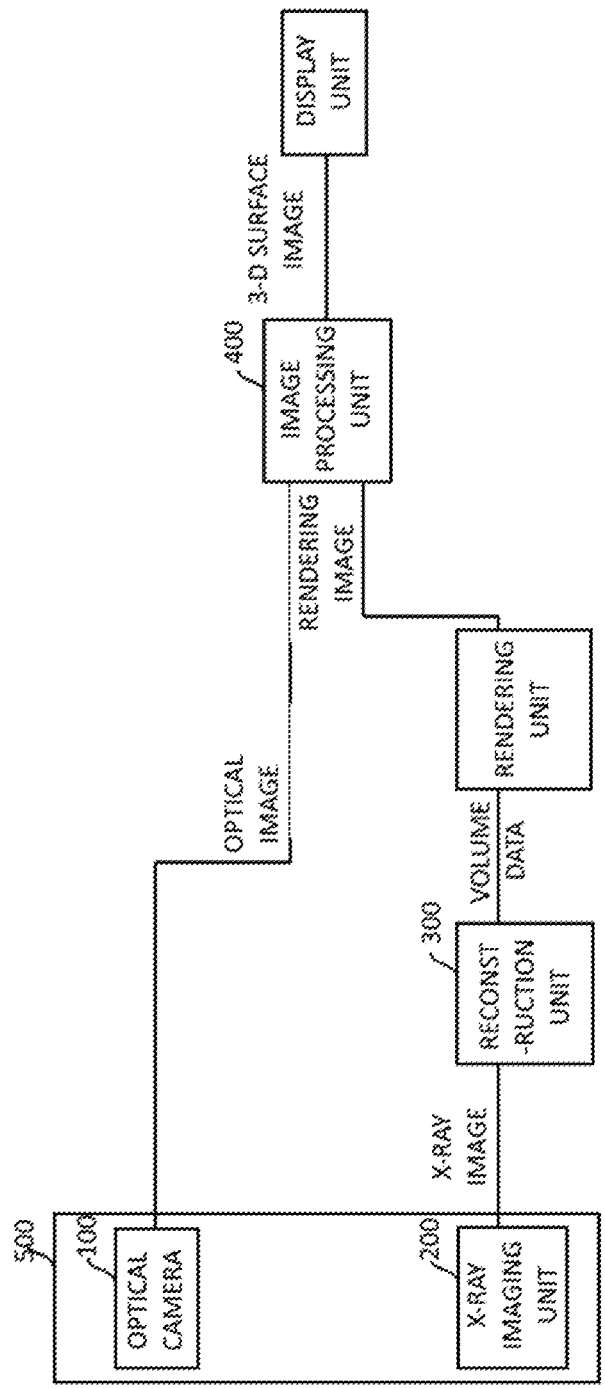
FIG. 2 is a block diagram of an apparatus for generating a three-dimensional surface image for dentistry in accordance with another embodiment of the present invention.

As shown in FIG. 2, the apparatus for generating a three-dimensional surface image for dentistry in accordance with another embodiment of the present invention further includes the rendering unit 310.

The rendering unit 310 generates a rendering image by rendering the volume data generated by the reconstruction unit 300. The rendering includes surface rendering or volume rendering. The rendering may be performed by various methods known in the image technology field.

In another embodiment of the present invention, the image processing unit 400 generates a three-dimensional surface image by registering a rendering image corresponding to the coordinate system of a target object with a three-dimensional optical image corresponding to the coordinate system of the target object. Furthermore, additionally, after registering the three-dimensional optical image with the rendering image, the image processing unit 400 may generate a more accurate three-dimensional surface image by registering the rendering image and a three-dimensional optical image when a distance deviation between the coordinate systems of the three-dimensional optical image and rendering image becomes a minimum again, while moving the coordinate system of the rendering image in a three-dimensional manner based on the three-dimensional optical image.

Furthermore, after registering a three-dimensional optical image and rendering image of a target object, the image processing unit 400 generates a three-dimensional surface image by substituting a different portion of the three-dimensional optical image with the boundary of the rendering image. In this case, the image processing unit 400 may properly adjust the color of the boundary portion of the substituted rendering image in order to minimize a difference between the boundary of the substituted rendering image and the remaining three-dimensional optical images other than the boundary of the substituted rendering image.

Figure 3:
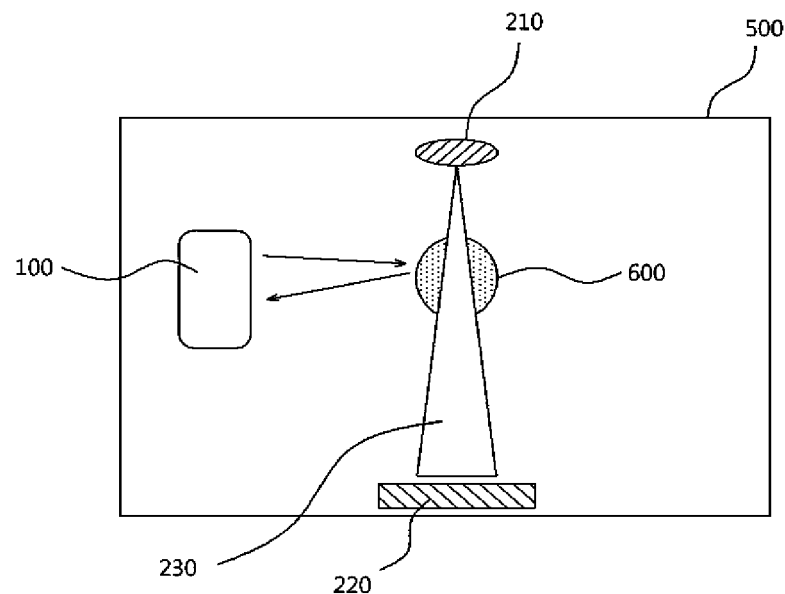
FIG. 3 is a diagram regarding the structure of an optical camera and an X-ray imaging unit within a three-dimensional imaging module in accordance with an embodiment of the present invention.
Figure 4:
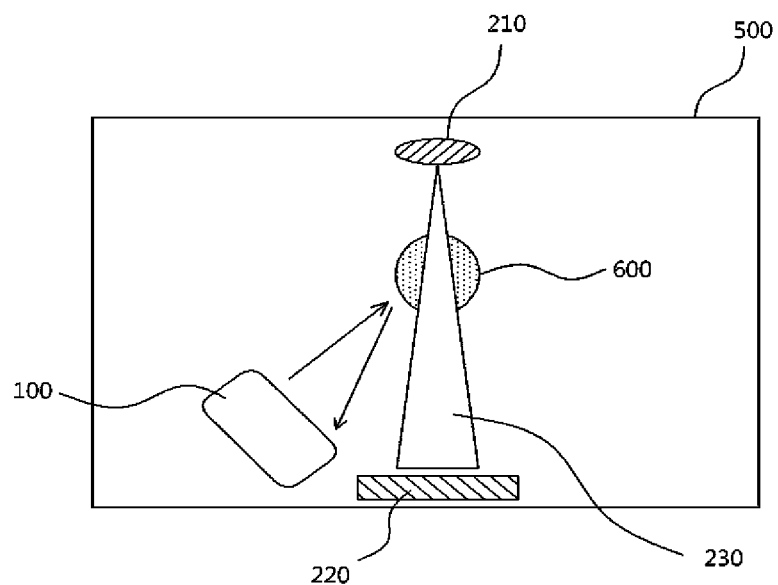
FIG. 4 is a diagram regarding the structure of an optical camera and an X-ray imaging unit within a three-dimensional imaging module in accordance with another embodiment of the present invention.
Figure 5:
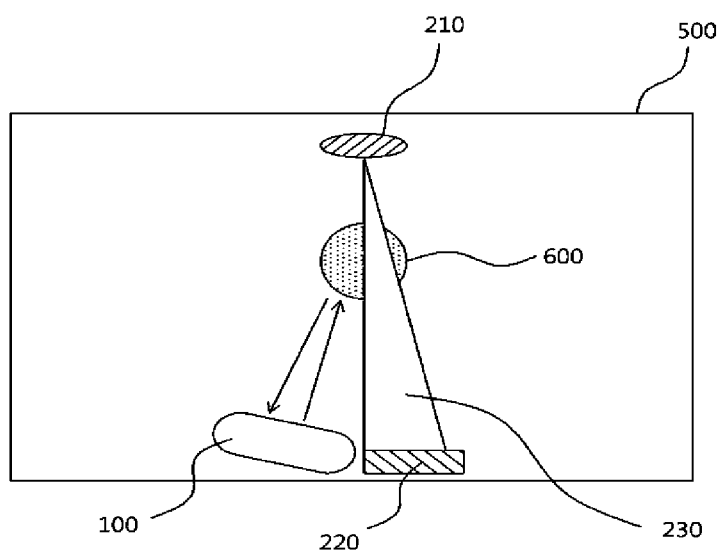
FIG. 5 is a diagram regarding the structure of an optical camera and an X-ray imaging unit within a three-dimensional imaging module in accordance with another embodiment of the present invention.

FIGS. 3 to 5 are diagrams regarding the structure of the optical camera 100 and the X-ray imaging unit 200 within the three-dimensional imaging module 500 in accordance with an embodiment of the present invention.

The three-dimensional imaging module 500 includes the optical camera 100, the X-ray emission source 210, the X-ray sensor 220, and the turn table 600. The three-dimensional imaging module includes the housing member for accommodating all of the optical camera, the X-ray emission source, the X-ray sensor, and the turn table and shielding X-rays 230 emitted from the X-ray emission source 210 to a target object.

The X-ray emission source 210 emits the X-rays 230 toward a target object placed on the turn table 600 and may emit the X-rays in a cone beam form. From FIGS. 3 and 4, it may be seen that the X-rays 230 are emitted by the X-ray emission source 210 in a cone beam form. From FIG. 5, it may be seen that the X-rays 230 are emitted by the X-ray emission source 210 in a half beam form. In this case, the X-rays 230 of the X-ray emission source 210 may be a fan beam, if necessary.

The X-ray sensor 220 faces the X-ray emission source 210 with the target object interposed therebetween in order to detect the X-rays 230 passing through the target object. A known X-ray sensor 220 including a gas detector, a TFT, or a flat panel detector of a CMOS method may be used as the X-ray sensor 220. The X-ray sensor 220 is not limited to a specific method.

The size of the X-ray sensor 220 is determined by a form of the X-rays 230 emitted by the X-ray emission source 210. If the X-ray emission source 210 emits the X-rays 230 in a half beam form, the size of the X-rays 230 may be half the size of the X-ray sensor 220 when the X-rays 230 are emitted in a cone beam form (refer to FIG. 5).

The turn table 600 is a portion on which the target object is placed, and is preferably rotated around an axis perpendicular to the radiation direction of the X-rays 230. Furthermore, the optical camera 100 is installed on one side of the target object.

As a result, in a process in which an impression material or a plaster cast into which the target object placed on the turn table 600, for example, a patient's dentition has been incorporated is rotated, the X-ray emission source 210 emits the X-rays 230 toward the target object. The X-rays passing through the target object are detected by the X-ray sensor 220. Accordingly, the projected data of the target object in multiple directions can be obtained. Furthermore, during the process, the optical camera 100 obtains optical images of the target object in the multiple directions. The optical camera 100 or the image processing unit 400 generates a three-dimensional optical image of the target object based on the optical images.

In this case, in order for the optical camera 100, the X-ray emission source 210, and the X-ray sensor 220 to be simultaneously within the three-dimensional imaging module 500, the optical camera 100, the X-ray emission source 210, and the X-ray sensor 220 need to be disposed by taking into consideration damage or interference between the optical camera 100 and the X-ray sensor 220. There is no special limit to the disposition other than the case where the optical camera 110 and the X-ray emission source 210 or the X-ray sensor 220 overlap.

That is, in FIGS. 3 and 4, the locations of the optical cameras 100 are different. In order to obtain the same three-dimensional optical image as a transmission image obtained by the X-ray imaging unit, it is preferred that the optical camera 100 is disposed near the X-ray sensor 220 as close as possible. However, the optical camera 100 may be disposed at a proper location within the housing member in order to prevent deterioration attributable to X-rays.

Furthermore, in an embodiment of the present invention, a target object has been illustrated as being rotated by the turn table 600, but an example in which the optical camera 100, the X-ray emission source 210, and the X-ray sensor 220 are rotated integrally or individually in the state in which the target object has been fixed may also be interpreted as belonging to the present invention.

What is claimed is:

1. An apparatus for generating a three-dimensional surface image for dentistry, the apparatus comprising:
    a three-dimensional imaging module comprising an optical camera obtaining a three-dimensional optical image of a target object and an X-ray imaging unit obtaining X-ray images of the target object in multiple directions;
    a reconstruction unit generating volume data by reconstructing the X-ray images;
    a rendering unit generating a rendering image of the target object by rendering the volume data; and
    an image processing unit generating the three-dimensional surface image of the target object by registering the three-dimensional optical image and the rendering image and substituting a different portion of the three-dimensional optical image with a boundary of the rendering image.

2. The apparatus of claim 1,
    wherein the three-dimensional imaging module comprises a turn table supporting the target object,
    wherein the optical camera is installed on one side of the target object and obtains the three-dimensional optical image using any one of a laser scan method, a confocal microscopy method, and a stereo photogrammetry method, and
    wherein the X-ray imaging unit comprises an X-ray sensor and an X-ray emission source with the target object interposed between the X-ray sensor and the X-ray emission source.

3. The apparatus of claim 1, wherein the image processing unit registers the three-dimensional optical image with the rendering image based on a coordinate system for the target object.

4. A method for generating a three-dimensional surface image for dentistry, the method comprising steps of:
    generating, by an optical camera, a three-dimensional optical image of a target object by imaging the target object in multiple directions;
    obtaining, by an X-ray imaging unit, X-ray images of the target object in multiple directions and generating volume data by reconstructing the X-ray images;
    generating a rendering image by rendering the volume data; and
    generating a three-dimensional surface image of the target object by registering the three-dimensional optical image and the rendering image and substituting a different portion of the three-dimensional optical image with a boundary of the rendering image.

* * * * *